(12) United States Patent
Tanter et al.

(10) Patent No.: US 10,974,080 B2
(45) Date of Patent: Apr. 13, 2021

(54) METHOD AND SYSTEM FOR SECURE INSONIFICATION OF LIVING TISSUES

(71) Applicants: CARDIAWAVE, Paris (FR); Ecole Supérieure de Physique et de Chimie Industrielles de la Ville de Paris, Paris (FR); INSERM (Institut National de la Santé et de la Recherche Médicale), Paris (FR); CENTRE NATIONAL DE LA RECHERCHE SCIENTIFIQUE—CNRS-, Paris (FR); Université Paris Diderot—Paris 7, Paris (FR)

(72) Inventors: Mickaël Tanter, Bagneux (FR); Mathieu Pernot, Paris (FR); Justine Robin, Paris (FR)

(73) Assignees: CARDIAWAVE, ECOLE SUPÉRIEURE DE PHYSIQUE, Paris (FR); INSERM, CNRS, UNIVERSITÉ PARIS DIDEROT—PARIS 7, Paris (FR)

( * ) Notice: Subject to any disclaimer, the term of this patent is extended or adjusted under 35 U.S.C. 154(b) by 274 days.

(21) Appl. No.: 15/899,076

(22) Filed: Feb. 19, 2018

(65) Prior Publication Data

US 2018/0236271 A1    Aug. 23, 2018

(30) Foreign Application Priority Data

Feb. 17, 2017 (EP) .................................... 17305179

(51) Int. Cl.
*A61N 7/02* (2006.01)
*A61N 7/00* (2006.01)
(Continued)

(52) U.S. Cl.
CPC .......... *A61N 7/02* (2013.01); *A61B 17/22004* (2013.01); *A61B 17/22029* (2013.01);
(Continued)

(58) Field of Classification Search
CPC .... A61N 7/00; A61N 7/02; A61N 2007/0004; A61B 2017/22007
See application file for complete search history.

(56) References Cited

U.S. PATENT DOCUMENTS

2006/0211958 A1 *   9/2006   Rosenberg .......... A61H 23/0236
                                                                601/9
2010/0298744 A1 * 11/2010   Altshuler .................. A61N 7/02
                                                                601/3
(Continued)

FOREIGN PATENT DOCUMENTS

WO    WO 2013/182800        12/2013
WO    WO 2016/156989 A1    10/2016

*Primary Examiner* — Jason M Ip
(74) *Attorney, Agent, or Firm* — von Briesen & Roper, s.c.

(57) ABSTRACT

A method and system for secure ultrasound treatment of living tissues using an ultrasound probe comprising a reflective cavity in acoustic communication with living tissues, a transducer to emit an ultrasound wave in the reflective cavity and a transducer to acquire a backscattered signal in the reflective cavity. The method comprises the steps of a) emitting a first ultrasound wave in the reflective cavity that generates a backscattered ultrasound wave in the reflective cavity, b) acquiring a backscattered signal in the reflective cavity, c) determining whether an insonification can be safely performed by computing a similarity value between the backscattered signal and a predefined reference signal, and d) if an insonification can be safely performed, treating the living tissues with a second ultrasound wave emitted in the reflective cavity. The second ultrasound wave is focused (Continued)

a target point of the living tissues and generates a pressure point resulting in cavitation at this target point.

15 Claims, 4 Drawing Sheets

(51) Int. Cl.
  *A61B 8/00* (2006.01)
  *A61B 17/22* (2006.01)
  *A61B 8/08* (2006.01)
  *A61B 17/00* (2006.01)

(52) U.S. Cl.
  CPC .............. *A61N 7/00* (2013.01); *A61B 8/4466* (2013.01); *A61B 8/485* (2013.01); *A61B 2017/00084* (2013.01); *A61B 2017/00243* (2013.01); *A61B 2017/00725* (2013.01); *A61B 2017/00783* (2013.01); *A61B 2017/22002* (2013.01); *A61B 2017/22007* (2013.01); *A61B 2017/22008* (2013.01); *A61B 2017/22014* (2013.01); *A61B 2017/22015* (2013.01); *A61B 2017/22028* (2013.01); *A61N 2007/0004* (2013.01); *A61N 2007/0039* (2013.01); *A61N 2007/0052* (2013.01); *A61N 2007/0069* (2013.01)

(56) References Cited

U.S. PATENT DOCUMENTS

| 2011/0054363 A1* | 3/2011 | Cain ........................ A61B 8/00 601/4 |
| 2013/0012838 A1* | 1/2013 | Jaeger ..................... A61B 8/56 601/2 |
| 2015/0065871 A1 | 3/2015 | Konofagou et al. |

* cited by examiner

METHOD AND SYSTEM FOR SECURE INSONIFICATION OF LIVING TISSUES

CROSS-REFERENCE TO RELATED APPLICATION

This application claims priority under the Paris Convention to European Patent Application No. 17305179.8 filed on Feb. 17, 2017.

TECHNICAL FIELD

The present disclosure relates to methods and systems for secure ultrasound treatment of living tissues.

BACKGROUND

More precisely, the disclosure relates to the field of ultrasound treatments of living tissues involving cavitation in the living tissues generated by focusing high intensity extremely short ultrasound pulses inside the tissues. An example of such treatments is histotripsy.

These techniques have been shown to allow for controlled modifications of the tissues, in particular controlled modifications of tissues elasticity, ranging from a softening of the tissues to an ablation of the treated tissues.

One example of recent developments in the field of cavitation-based ultrasound treatments is known from document WO 2013/182800 which describes a device able to focus high intensity extremely short ultrasound pulses inside living tissues. This device comprises an array of transducers adapted to emit, into a reflective cavity, ultrasound waves focused on a target point of an external medium such as living tissues. By making use of internal reflection inside the reflective cavity high intensity pulses can be focused on a target point and result in pressure pulses sufficient to generate cavitation in the medium.

A promising application of such ultrasound treatment is, among others, the treatment of valvular stenosis in which the cardiac valve leaflets are known to become stiffer.

The stiffening of cardiac valve leaflets narrows the valve opening and reduces the amount of blood that can flow through it. A controlled softening of the leaflet tissues allows for a reopening of the cardiac valves.

Preliminary studies have shown great potential for cavitation based techniques as a therapy tool for non-invasive treatment of valvular stenosis.

Cavitation-based techniques differ in particular from High Intensity Focused Ultrasound ("HIFU") treatments. In HIFU treatments, high energy long duration ultrasound waves are used to heat tissues over their liquefaction temperatures in order to ablate tissues or to change their properties. However, heating tissues to such temperatures can be difficult and dangerous in living tissues since the tissues are bathing in blood and body liquid and are thus thermally stabilized at 98.6° F. (37° C.).

Indeed, a particularly interesting feature of cavitation-based techniques is the possibility to perform the ultrasound treatment on living tissues and in particular on tissues of functioning organs, for instance on tissues of a beating heart.

This way, a cardiopulmonary bypass of the patient may be avoided thereby strongly reducing the risk of serious complications. Moreover, a large class of older patients who are excluded from the scope of current surgery-based medical treatments (open surgery or catheter-based surgery) may become eligible to cavitation-based techniques.

However, treating living tissues and in particular tissues of functioning organs implies stringent requirements regarding the level of safety of the cavitation-based method and systems.

There is thus a need for methods and systems for ultrasound treatment of living tissues that could be operated on living tissues and functioning organs and involve a less invasive medical intervention while guaranteeing a high level of safety, a high precision and a strong reliability of operation.

One object of the present disclosure is to improve this situation.

SUMMARY

To this aim, a first object of the disclosure is a method for secure ultrasound treatment of living tissues, the method comprising providing an ultrasound probe comprising a reflective cavity able to be in acoustic communication with living tissues to transmit ultrasound wave to said living tissues, at least one transducer able to emit an ultrasound wave in the reflective cavity and at least one transducer able to acquire a backscattered signal in the reflective cavity, the method further comprising at least the successive steps of:

a) emitting at least one first ultrasound wave in the reflective cavity by controlling at least one transducer of the ultrasound probe, said first ultrasound wave generating a backscattered ultrasound wave in the reflective cavity, b) acquiring a backscattered signal in response to the backscattered ultrasound wave in the reflective cavity by controlling at least one transducer of the ultrasound probe, c) determining whether an insonification can be safely performed by:

computing a similarity value between said backscattered signal and a predefined reference signal, comparing said similarity value with a security threshold to determine whether an insonification can be safely performed, d) if it is determined that an insonification can be safely performed, treating the living tissues by controlling at least one transducer of the ultrasound probe to emit at least one second ultrasound wave in the reflective cavity, said at least one second ultrasound wave being transmitted to the living tissues, focused on at least one target point of the living tissues and generating a pressure pulse sufficient to result in cavitation at said at least one target point.

In addition, one may also use one or more of the following features:

the predefined reference signal is selected in a predefined reference signal database associating predefined reference signals with temperatures of the reflective cavity;

the method further comprises a step of measuring a temperature of the reflective cavity using a thermometer, preferably the predefined reference signal is selected in the predefined reference signal database based on the measured temperature;

the at least one second ultrasound wave is emitted by driving at least one transducer of the ultrasound probe with a predefined treatment signal, and the predefined treatment signal is selected in a predefined treatment signal database associating predefined treatment signals with temperatures of the reflective cavity, preferably the predefined treatment signal is selected in the predefined treatment signal database based on the measured temperature;

said at least one first ultrasound wave does not generate a pressure pulse sufficient to result in cavitation in the living tissues, preferably said at least one first ultrasound wave is not transmitted to the living tissues, in particular prior to a therapeutic procedure;

said at least one first ultrasound wave is transmitted to the living tissues, focused on at least one target point of the living tissues, preferably said at least one first ultrasound wave generates a pressure pulse sufficient to result in cavitation at said at least one target point, in particular during a therapeutic procedure;

said similarity value between said backscattered signal and a predefined reference signal is indicative of a presence of forbidden tissues in a region of the living tissues penetrated by said at least one first ultrasound wave, such as lung tissues;

said predefined reference signal is indicative of a cavitation at said at least one target point of the living tissues resulting from a pressure pulse generated by said at least one first ultrasound wave;

said predefined reference signal is function of a backscattered signal acquired in at least one previous insonification, said previous insonification being performed prior to the step of emitting at least one first ultrasound wave in the reflective cavity, said previous insonification comprising emitting at least one ultrasound wave in the reflective cavity by controlling at least one transducer of the ultrasound probe, said at least one ultrasound wave being transmitted to the living tissues and focused on at least one target point of the living tissues, said at least one ultrasound wave generating a backscattered ultrasound wave in the reflective cavity, and acquiring a backscattered signal in response to said backscattered ultrasound wave in the reflective cavity by controlling at least one transducer of the ultrasound probe, preferably said predefined reference signal is function of an average of a plurality of backscattered signals acquired from a respective plurality of previous insonifications;

a multiple scattering of ultrasound waves in the reflective cavity is caused by a multi-diffusing medium located in said reflective cavity, in particular a multiple scattering of at least the first ultrasound wave and the second ultrasound wave;

at least the second ultrasound wave is transmitted in the living tissues through a window formed in the reflective cavity;

at least the second ultrasound wave is emitted by driving at least one transducer of the ultrasound probe with a predefined treatment signal whose duration is less than 10 milliseconds, preferably less than 1 millisecond, in particular the duration of said predefined treatment signal is at least 10 times longer than the duration of pressure pulse generated by the second ultrasound wave at at least one target point of the living tissues, preferably at least 50 times longer than said duration;

said at least one second ultrasound wave generates at the at least one target point of the living tissues a peak negative pressure halfcycle that exceeds a peak negative pressure of 5 MPa and/or a peak positive pressure halfcycle that exceeds a peak positive pressure of 20 MPa, in particular at least the first ultrasound wave and the second ultrasound wave generate at at least one target point of the living tissues peak negative pressure halfcycles that exceed a peak negative pressure of 5 MPa and/or peak positive pressure halfcycles that exceeds a peak positive pressure of 20 MPa;

the duration of a pressure pulse generated by each second ultrasound wave of the sequence of second ultrasound waves is less than 50 microseconds, preferably less than 10 microseconds;

the step d) of treating the living tissues comprises controlling at least one transducer of the ultrasound probe to successively emit a sequence of second ultrasound waves in the reflective cavity, said second ultrasound waves being transmitted to the living tissues, respectively focused on a plurality of respective target points of the living tissues, said second ultrasound waves being electronically steered to scan a treatment region of the living tissues formed by said plurality of target points, preferably the sequence of steps a), b), c), d) is reiterated at least once.

Another object of the disclosure is a method for calibrating a system for secure ultrasound treatment of living tissues, the method comprising providing an ultrasound probe comprising a reflective cavity in acoustic communication with living tissues and able to transmit ultrasound wave to said living tissues, at least one transducer able to emit an ultrasound wave in the reflective cavity and at least one transducer able to acquire a backscattered signal in the reflective cavity, the method further comprising at least the successive steps of:

a) adjusting a temperature of the reflective cavity to a predefined temperature, b) emitting at least one first ultrasound wave in the reflective cavity by controlling at least one transducer of the ultrasound probe, said first ultrasound wave generating a backscattered ultrasound wave in the reflective cavity, c) acquiring a backscattered signal in response to the backscattered ultrasound wave in the reflective cavity by controlling at least one transducer of the ultrasound probe, d) determining a predefined reference signal function of said backscattered signal and storing said predefined reference signal associated with the predefined temperature in a database associating predefined reference signals with temperatures of the reflective cavity.

Yet another object of the disclosure is a system for secure ultrasound treatment of living tissues, said system comprising:

an ultrasound probe comprising a reflective cavity able to be in acoustic communication with living tissues to transmit ultrasound wave to said living tissues, at least one transducer able to emit an ultrasound wave in the reflective cavity and at least one transducer able to acquire a backscattered signal in the reflective cavity, a control and safety system specially adapted for:

controlling at least one transducer of the ultrasound probe to emit at least one first ultrasound wave in the reflective cavity, said first ultrasound wave generating a backscattered ultrasound wave in the reflective cavity, controlling at least one transducer of the ultrasound probe to acquire a backscattered signal in response to the backscattered ultrasound wave in the reflective cavity, determining whether an insonification can be safely performed by computing a similarity value between said backscattered signal and a predefined reference signal, and comparing said similarity value with a security threshold to determine whether an insonification can be safely performed, controlling at least one transducer of the ultrasound probe to emit at least one second ultrasound wave in the reflective cavity if it is determined that an insonification can be safely performed, said at least one second ultrasound wave being transmitted in the living tissues, focused on at least one target point of the living tissues and generating a pressure pulse sufficient to result in cavitation at said at least one target point.

BRIEF DESCRIPTION OF THE DRAWINGS

Other characteristics and advantages will readily appear from the following description of several embodiments, provided as non-limitative examples, and of the accompanying drawings.

On the drawings.

On the different Figures, the same reference signs designate like or similar elements.

DETAILED DESCRIPTION

Figure 1:
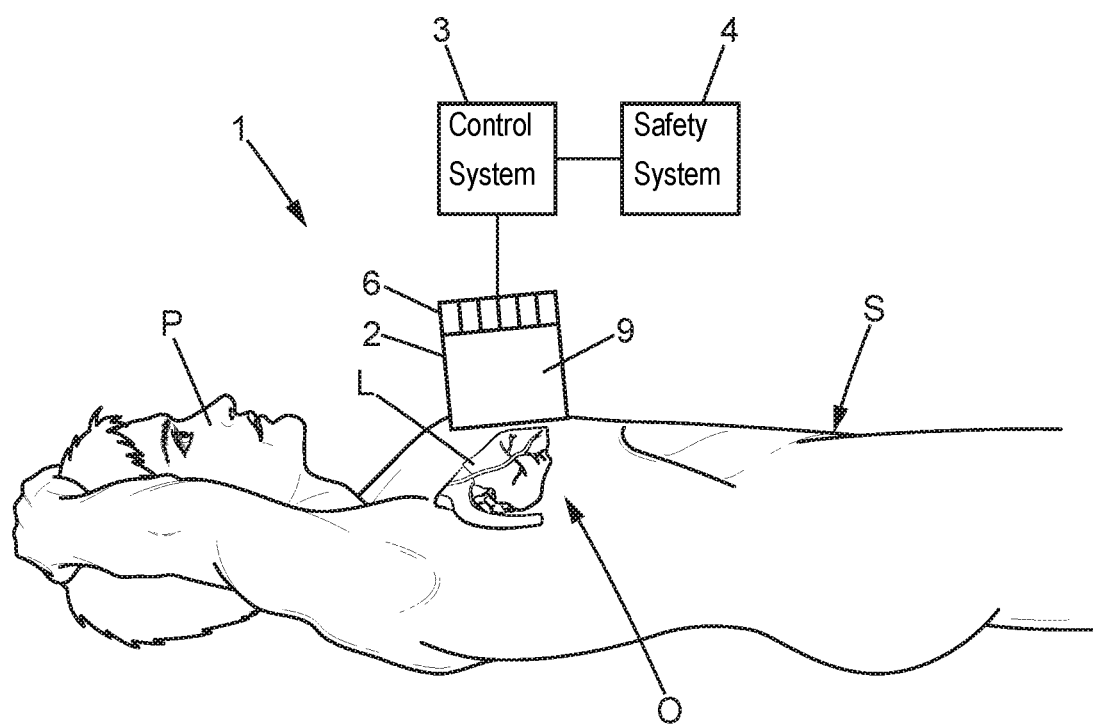
FIG. 1 illustrates a system for secure ultrasound treatment of living tissues according to an embodiment of the invention.

FIG. 1 illustrates a system 1 for secure ultrasound treatment of living tissues L according to an embodiment.

The living tissues L may be for instance tissues of an organ O. The patient may be a mammalian, for instance a human.

In one particularly interesting embodiment of the invention, the organ O is a heart of a patient. In this embodiment, the safety of the insonification of the heart is critical.

Living tissues L may be tissues of a functioning organ O, in particular a beating heart.

By "functioning organ", it is meant that the organ is located inside the body of the patient and in particular that the organ is not bypassed from the patient bloodstream.

The system 1 comprises an ultrasound probe 2. The ultrasound probe 2 may be located externally to the organ O or to the body of the patient P and arranged to be able to produce ultrasound waves focused inside said organ O.

As illustrated on FIG. 1, the ultrasound probe 2 can be arranged externally to the patient and, for instance, in contact with the skin S of the patient P, in particular close to the organ O of the patient, for instance the heart of the patient P. This way, the method according to the invention may be non-invasive.

In a variant, non-illustrated on the drawings, the skin and/or bones of the patient may be pushed aside during a preliminary surgical operation so that the ultrasound probe 2 can be arranged in closer proximity to the organ O. The ultrasound probe 2 may also be introduced under the skin and/or bones of the patient to be arranged in close proximity to the organ O.

Figure 2:
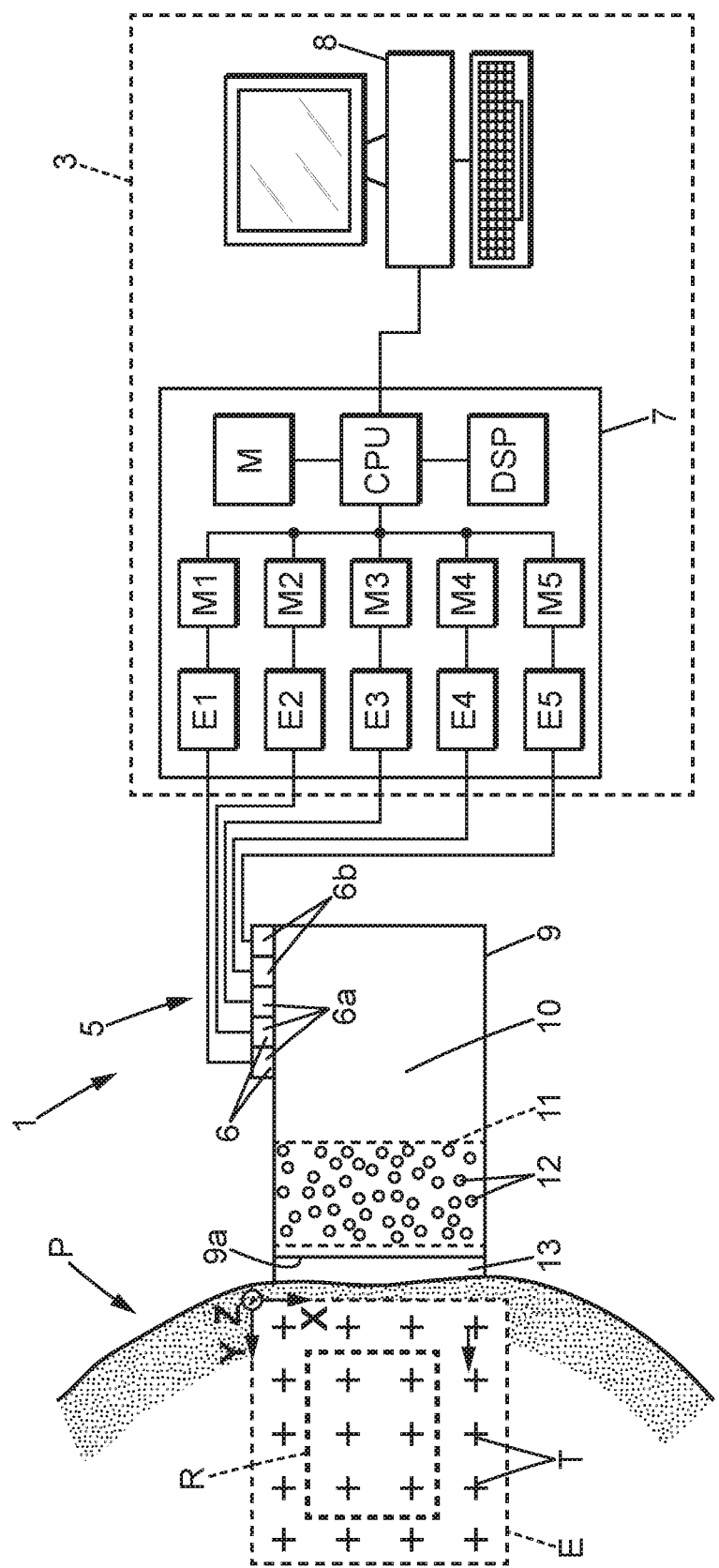
FIG. 2 illustrates a detail of the ultrasound probe of the system of FIG. 1 according to one embodiment of the invention.

As shown on FIGS. 1 and 2, the ultrasound probe 2 comprises a reflective cavity 9 able to be in acoustic communication with living tissues L to transmit ultrasound waves to said living tissues L.

The ultrasound probe 2 also comprises at least one transducer 6 able to emit an ultrasound wave in the reflective cavity 9 and at least one transducer 6 able to acquire a backscattered signal in the reflective cavity 9.

In one embodiment of the invention, the same transducer 6, or array 5 of transducers 6, may be used to emit ultrasound waves and to acquire signal from the reflective cavity, in particular to emit the first ultrasound wave and to acquire the backscattered signal detailed further below.

In another embodiment, first transducers 6a may be used to emit ultrasound waves and second transducers 6b may be used to acquire signals.

This way, simultaneous emission and acquisition may be performed.

There can be any number of transducers 6, ranging from 1 to several hundred, for example several tens of transducers.

Transducers 6 may be arranged in one or several array(s) 5. The arrays 5 may be linear arrays, with the transducers juxtaposed side by side along a longitudinal axis of the array. The arrays 5 may also be two-dimensional arrays so as to emit three-dimensional focused waves.

The ultrasound probe 2 further comprises a control and safety system 3, 4. The control and safety system 3, 4 is shown in FIG. 1 as constituted by two assemblies, to with a control system 3 and a safety system 4, but such control and safety system 3, 4 could be constituted of one single unit or assembly, or more than two assemblies. The control system 3 is specially adapted for controlling at least one transducer 6 of the ultrasound probe 2 to emit ultrasound waves in the reflective cavity 9 and to acquire signal in response to ultrasound wave in the reflective cavity 9.

The control system 3 may comprise for instance:

an electronic system 7 able to command the transducer(s) 6 to fire ultrasound waves and to acquire ultrasound signals; and a microcomputer 8 for controlling the electronic system 7.

As shown on FIG. 2, the electronic system 7 may include for instance:

n digital/analog converters ($E_1$-$E_n$) individually connected to n transducers 6 ($T_1$-$T_n$) of the array 5;

n buffer memories ($M_1$-$M_n$) respectively connected to the n digital/analog converters, a central processing unit (CPU) communicating with the buffer memories and the microcomputer 8, a memory (M) connected to the central processing unit;

a digital signal processor (DSP) connected to the central processing unit.

Several transducers 6 ($T_1$-$T_n$) of the array 5 can thus be controlled independently of one another by the central processing unit of the electronic system 7 by driving the transducers with appropriate driving signals.

Figure 3:
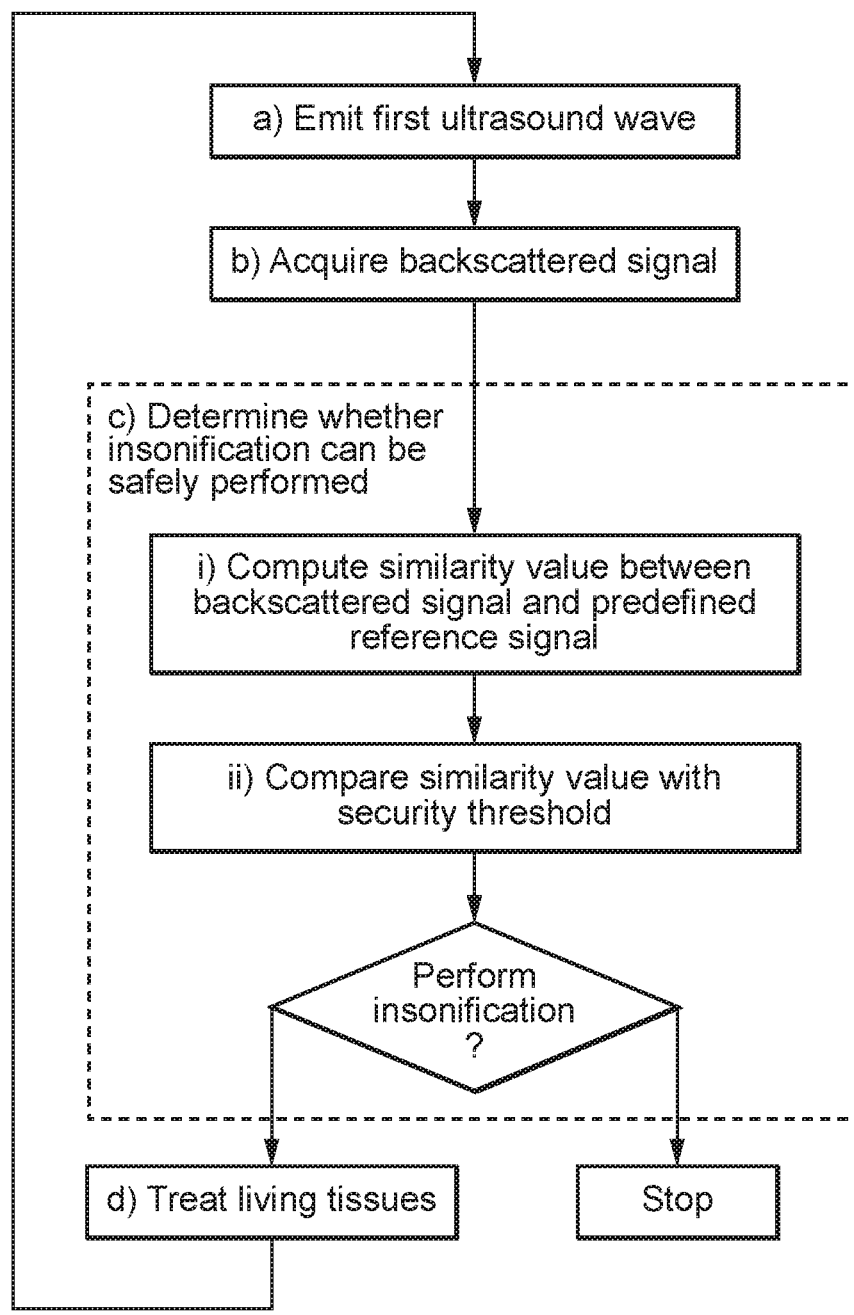
FIG. 3 is a flowchart of a method for secure ultrasound treatment of living tissues according to an embodiment of the invention.

As illustrated on FIG. 3, the control system 3 is in particular able to emit at least one first ultrasound wave in the reflective cavity 9 during a step a of the method according to the invention.

In one embodiment, the first ultrasound wave may not generate a pressure pulse sufficient to result in cavitation in the living tissues L. The first ultrasound wave may then not be used to perform ultrasound treatment of the living tissues but may rather be used to control the proper functioning of the cavity.

Advantageously, said first ultrasound wave may not even be transmitted to the living tissues. The ultrasound probe 2 may for instance not be in contact with the living tissues L or with the patient P when the first ultrasound wave is emitted.

In a second embodiment, the at least one first ultrasound wave may be transmitted to the living tissues. The first ultrasound wave may be transmitted in the living tissues L through the window 7b formed in the reflective cavity 9 as detailed above.

In particular, the first ultrasound wave may be focused on at least one target point T of the living tissues L. The first ultrasound wave may even generate a pressure pulse sufficient to result in cavitation at said at least one target point T. In this embodiment, the first ultrasound wave may thus be able to perform a treatment of the living tissues.

In this description, it is thus meant by "treatment of the living tissues", "treating the living tissues", "insonification" or "insonificating", a step or a process during which an ultrasound wave is focused on at least one target point of the living tissues and generates a pressure pulse sufficient to result in cavitation at said at least one target point T.

In all embodiments, the first ultrasound wave generates a backscattered ultrasound wave in the reflective cavity 9.

When the ultrasound probe 2 is not in contact with the living tissues L and the first ultrasound wave not transmitted to the living tissues, the backscattered ultrasound wave simply consists of the first ultrasound wave and its reflections inside the reflective cavity 9. When the ultrasound probe 2 is in contact with the living tissues L and the first ultrasound wave is transmitted to the living tissues, the backscattered ultrasound wave may further comprise at least some portion of an ultrasound wave generated in the living tissues by the first ultrasound wave and propagating back in the reflective cavity 9. The ultrasound wave generated in the living tissues by the first ultrasound wave may be for instance a portion of the first ultrasound wave reflected by scatterers in the living tissues or an ultrasound wave generated by the pressure pulse at the target point T.

As illustrated on FIG. 3, the control system 3 is also able to acquire a backscattered signal in response to the backscattered ultrasound wave in the reflective cavity 9 by controlling at least one transducer 6 of the ultrasound probe 2 during a step b of a method according to the invention.

In one embodiment, the backscattered signal may directly correspond to a signal recorded by transducers 6 in response to the backscattered ultrasound wave in the reflective cavity 9.

Alternatively, the signal recorded by transducers 6 may be filtered and processed to determine the backscattered signal.

For instance, the signal recorded by transducers 6 may be filtered in order to keep only a relevant part of the recorded signal. The relevant part of the recorded signal may for instance be a coda following a first pulse in the recorded signal with a typical duration ranging between 50 μs and 3 ms.

The signal received by transducers 6 may also be further processed in order to determine the backscattered signal. For instance, an energy of the recorded signal, in a predefined frequency range typically ranging between 0.3 MHz and 5 MHz and a typical central frequency around 1 MHz and/or in a predefined time span, may be computed and may form the backscattered signal.

As a matter of example, the backscattered signal may thus for instance correspond to the energy in the coda of a signal recorded by transducers 6 in response to the backscattered ultrasound wave in the reflective cavity 9.

The safety system 4 is adapted for determining whether an insonification can be safely performed.

The safety system 4 comprises for instance a computer or general processing unit and/or a signal processing chip.

As illustrated on FIG. 3, such a step c) of determination of a method according to the disclosure, comprises at least the operations of (i) computing a similarity value between the backscattered signal and a predefined reference signal, and (ii) comparing said similarity value with a security threshold to determine whether an insonification can be safely performed.

These two operations will now be further detailed in relation with several embodiments.

To emit the at least one first ultrasound wave, the means for controlling 3 drive at least one transducer 6 of the ultrasound probe 2 with a predefined emission signal.

The predefined emission signal may be recorded in a memory of the system, for instance the memory M connected to the central processing unit.

In a first embodiment, the predefined emission signal may be a reference code predetermined to control the properties of the cavity and the stability over time of the ultrasound probe itself.

In this embodiment, the first ultrasound wave may thus not generate a pressure pulse sufficient to result in cavitation in the living tissues, and may even not be transmitted to the living tissues. The step of emitting the first ultrasound wave may then not be considered as a treatment of the living tissues.

Such a reference code can be predetermined so that small changes in the properties of the reflecting cavity, for instance dilatations or modifications in the reflecting coefficients of the cavity walls, will be converted in noticeable changes in the backscattered waves and thus measurable changes in the backscattered signal versus predefined reference signal.

Indeed, it has been discovered by the inventors that the properties of the reflecting cavity 9 can be strongly affected by the operating temperature and have a strong impact on the proper functioning of the treatment system.

In this embodiment, the predefined reference signal can for instance be selected in a predefined reference signal database associating predefined reference signals with temperatures of the reflective cavity and, if necessary with predefined emission signal.

The operational temperature of the reflecting cavity can also be inferred from the predefined reference signal database by performing one or several comparisons of the backscattered signal with predefined reference signals stored in the predefined reference signal database.

Alternatively or in addition, the ultrasound probe 2 may further comprise a thermometer 14 (not shown) able to measure a temperature of the reflective cavity 9.

The predefined reference signal to be used in the method may then be selected in the database based on the temperature measured by the thermometer 14 or based on the temperature inferred from the predefined reference signal database.

If the backscattered signal and the predefined reference signal differ from one another, more than a security margin, it may then be decided not to perform an insonification but to recalibrate the cavity or to investigated the reason for such a strong departure from the nominal properties of the cavity.

To this aim, a similarity value between the backscattered signal and the predefined reference signal may be computed.

For instance, the similarity value may be defined as a normalized correlation R between the backscattered signals $s(k)$ and the reference backscattered signals $s_0(k)$.

$$R = \sum_{k=0}^{N} \frac{s_0(k) * s(k)}{\sqrt{\sum s_0(k)^2 \sum s(k)^2}}$$

Figure 5:
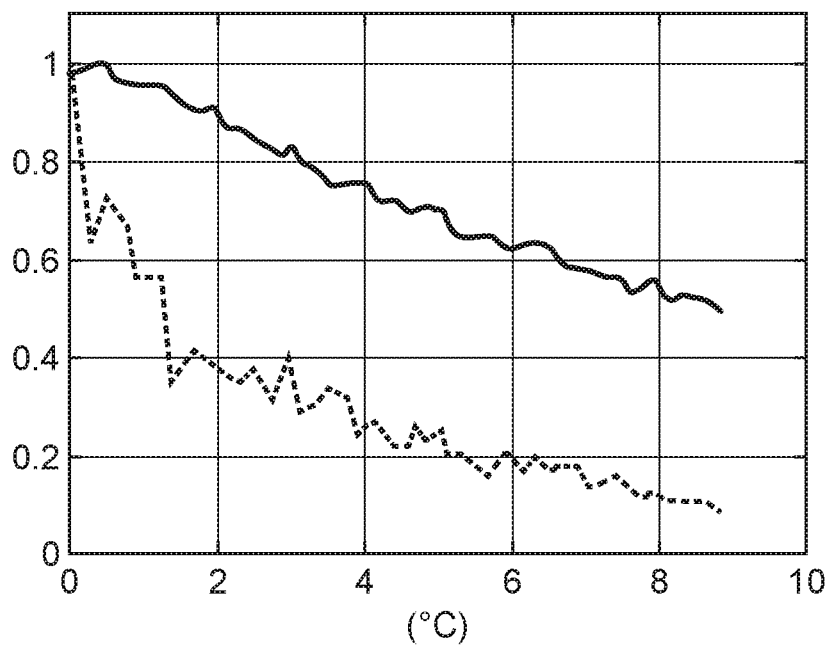

The similarity value may then be compared with a security threshold typically set to 0.5 (ranging between 0.3 and 1 depending on the security level required or on the maximum accepted decrease in the focal pressure) to determine whether an insonification can be safely performed. In typical experimental configurations, a decrease of about 5% in the maximum pressure at focus (continuous line on FIG. 5) leads to an autocorrelation value of about 0.5 (dashed line on FIG. 5). The autocorrelation value can thus be highly sensitive to the parameters of the insonification.

Alternatively, the similarity value R can be defined as a mean absolute difference between signals such as:

$$R = \frac{1}{N} \sum \text{abs}(s_0(k) - s(k))$$

In other embodiments, could the similarity value R may be defined as a time averaged standard deviation R:

$$R = \sqrt{\frac{1}{N} \sum (s_0(k) - s(k))^2}$$

In a variant or in addition, the measured or inferred temperature may also be compared to a threshold value to determine whether an insonification can be safely performed. If the operational temperature of the reflecting cavity is too high for instance, the insonification may be prevented since the cavity's properties may then not be nominal.

If it is determined that an insonification can be safely performed, the method may then comprise a step d) of treating the living tissues as illustrated on FIG. 3.

To this aim, the control system 3 can then control at least one transducer 6 of the ultrasound probe 2 to emit at least one second ultrasound wave in the reflective cavity 9. The second ultrasound wave is transmitted to the living tissues L, for instance through the window 7b formed in the reflective cavity 9. The second ultrasound wave is focused on at least one target point T of the living tissues L. The at least one second ultrasound wave generates a pressure pulse sufficient to result in cavitation at said at least one target point T.

To emit the at least one second ultrasound wave, the means for controlling 3 may drive at least one transducer 6 of the ultrasound probe 2 with a predefined treatment signal.

The predefined treatment signal may be recorded in a memory of the system, for instance the memory M connected to the central processing unit.

In one embodiment, the predefined treatment signal is selected in a predefined treatment signal database associating predefined treatment signals with temperatures of the reflective cavity.

The predefined treatment signal to be used may then be selected in said predefined treatment signal database based on the temperature measured by the thermometer 14.

The predefined treatment signal to be used may also be selected in said predefined treatment signal database based on a temperature of the reflective cavity deduced from a comparison of the backscattered signal with the predefined reference signal stored in the predefined reference signal database as mentioned before.

In a second embodiment that may be combined with the first embodiment, the first ultrasound wave may be used for controlling the safety of treatment of the living tissues.

In this embodiment, the at least one first ultrasound wave may then be transmitted to the living tissues, in particular transmitted in the living tissues L through the window 7b formed in the reflective cavity 9 as detailed above.

In a first variant of this embodiment, the predefined reference signal can be indicative of a presence of forbidden tissues in a region of the living tissues penetrated by said at least one first ultrasound wave, for instance lung tissues.

By "forbidden tissues", it is meant tissues of the patient P that are not intended to be insonificated, in particular since these tissues may be fragile or sensitive to ultrasound waves. On example of forbidden tissues are lung tissues, in particular in the case of heart tissues treatment. In cavitation-based treatment of the heart or of an organ located close to the lung, it is very important to ensure that there is no damage caused to the lung during the treatment. One of the aims of the present invention is thus to reduce this kind of hazard.

In this embodiment also, the predefined reference signal may be selected in a predefined reference signal database associating predefined reference signals with at least one predefined emission signal and a plurality of temperatures of the reflective cavity.

The predefined reference signal may be a pre-calibrated backscattered signal corresponding to a backscattered signal that is expected for normal operation through an organ O such as the heart.

To this aim, a predefined reference signal may be predetermined from a backscattered signal acquired in response to controlled ultrasound waves travelling along an optimal path through the living tissues, or may be pre-computed to correspond to a backscattered signal acquired in response to controlled ultrasound waves travelling along an optimal path through the living tissues.

A similarity value between the backscattered signal and the predefined reference signal may then be computed.

If the backscattered signal and the predefined reference signal differ from one another, more than a security margin, the similarity value between said backscattered signal and a predefined reference signal may then be indicative of a presence of forbidden tissues in a region of the living tissues penetrated by said at least one first ultrasound wave.

A security threshold can be predetermined from the security margin and the similarity value between the backscattered signal and the predefined reference signal can be compared to the security threshold during the method according to the invention.

In this variant, the at least one first ultrasound wave may be an ultrasound wave focused on a target point of the living tissues.

The first ultrasound wave may also be an unfocused ultrasound wave. This way, it may be possible to penetrate a larger region of the living tissues that the region penetrated by the ultrasound waves used for the insonification, in order to better assess the safety of the insonification.

Alternatively, the predefined reference signal may be predetermined from a backscattered signal acquired in response to controlled ultrasound waves corresponding to forbidden operations.

By "forbidden operations", it is mean insonification through forbidden tissues, i.e. with ultrasound wave penetrating the lung for instance or focused in the lung tissues.

The backscattered signal may then be predetermined from a backscattered signal acquired in response to controlled ultrasound waves travelling through forbidden tissues, for instance travelling through lung tissues, or may be pre-computed to correspond to a backscattered signal acquired in response to controlled ultrasound waves travelling through forbidden tissues.

In this alternative, if the backscattered signal and the predefined reference signal correspond to one another, again given a predefined security margin, the similarity value between said backscattered signal and a predefined reference signal is then indicative of a presence of forbidden tissues in a region of the living tissues penetrated by said at least one first ultrasound wave.

Depending on the result of the comparison between the similarity value and the predefined threshold, it may thus be decided not to perform an insonification but to move the ultrasound probe to a proper location or to investigated the reason for such a presence of forbidden tissues in the insonification region.

In a second variant of the second embodiment, that may be combined with the previously described variants and embodiments, the predefined reference signal may be indicative of a cavitation at a target point of the living tissues where the first ultrasound wave is focused.

Said cavitation may in particular result from a pressure pulse generated by a first ultrasound wave.

Here again, a predefined reference signal may be predetermined from a backscattered signal acquired in response to controlled ultrasound waves focused on at least one target point of the living tissues and generating a pressure pulse sufficient to result in cavitation at said at least one target point. The predefined reference signal may also be pre-computed to correspond to a backscattered signal acquired in response to controlled ultrasound waves focused on at least one target point of the living tissues and generating a pressure pulse sufficient to result in cavitation at said at least one target point.

In this variant, the at least one first ultrasound wave may be transmitted to the living tissues, and may in particular be focused on at least one target point of the living tissues in order to generate a pressure pulse sufficient to result in cavitation at said at least one target point.

In this embodiment, the step a) of emitting at least one first ultrasound wave may thus be a step of treating the living tissues.

A similarity value between the backscattered signal and the predefined reference signal may again be computed and compared with a security threshold.

If the backscattered signal and the predefined reference signal differ from one another, more than a security margin, it may then be concluded that the first ultrasound wave did not result in cavitation at the target point T. The system 1 may then determine not to perform further insonifications but to stop the treatment in order to investigate the cause of such an absence of cavitation.

In a third variant of the second embodiment, that may be combined with the previously described variants, the predefined reference signal may be function of a backscattered signal acquired in at least one previous insonification.

The previous insonification is performed prior to the step (step a) of emitting at least one first ultrasound wave in the reflective cavity.

The previous insonification comprises a step of emitting at least one ultrasound wave in the reflective cavity. This emission is performed by controlling at least one transducer 6 of the ultrasound probe 2 by the means of controlling 3. The at least one ultrasound wave is transmitted to the living tissues as mentioned above and focused on at least one target point T of the living tissues L. In particular, the ultrasound wave may generate a pressure pulse sufficient to result in cavitation at said at least one target point. The ultrasound wave also generates a backscattered ultrasound wave in the reflective cavity as detailed above.

The previous insonification also comprises a step of acquiring a backscattered signal in response to said backscattered ultrasound wave in the reflective cavity. This acquisition may also be performed by controlling at least one transducer 6 of the ultrasound probe 2 by the means of controlling 3 as detailed above.

The previous thus correspond to step a and step b of the method of the invention with the particularity that the ultrasound wave emitted during step a are focused on at least one target point of the living tissues L and can generate a pressure pulse sufficient to result in cavitation at said at least one target point.

In one variant, the predefined reference signal can be function of an average of a plurality of backscattered signals acquired from a respective plurality of previous insonifications.

Each previous insonification of this plurality of previous insonification may be as performed as detailed above, the resulting backscattered signals being averaged together to determine a predefined reference signal.

In this third variant also, the at least one first ultrasound wave may be transmitted to the living tissues, and may in particular be focused on at least one target point of the living tissues in order to generate a pressure pulse sufficient to result in cavitation at said at least one target point.

The step a) of emitting at least one first ultrasound wave may thus be a step of treating the living tissues.

A similarity value between the backscattered signal and the predefined reference signal may again be computed and compared with a security threshold.

If the backscattered signal and the predefined reference signal differ from one another, more than a security margin, it may then be concluded that the step of treating the living tissues by emitting the first ultrasound wave did not result in a backscattered signal similar to the signal of the previous insonification(s) that is stored in the predefined reference signal.

The system 1 may thus determine not to perform further insonifications but to stop the treatment in order to investigate the cause of such a deviation from the previous insonification(s).

Several insonifications may be performed, separated by steps of determining whether an insonification can be safely performed to control the safety of operation.

In some embodiments of the invention, during the step of treating the living tissues, the ultrasound probe 2 successively emit a sequence of second ultrasound waves. The second ultrasound waves may then be transmitted to the living tissues and be respectively focused on a plurality of respective target points of the living tissues.

The sequence of second ultrasound waves may in particular be such that the focal spots of the sequence of N focused ultrasound waves scan a treatment region R of the living tissues.

By "scan the entire treatment region", it is meant that the centres of the focal spots of the sequence of N focused ultrasound waves are arranged to fill the entire treatment region R with a given minimal distance separating the centre of each focal spots and a given maximal distance separating the centre of each focal spots from its nearest neighbour.

By using such a sequence of N focused ultrasound waves, it is possible for instance to soften the living tissues while preventing ablation of said tissues.

As mentioned above, the ultrasound probe 2 is in particular able to emit focused ultrasound wave that generates a pressure sufficient to result in cavitation forming a bubble cloud at a focal spot of the focused ultrasound wave.

Such acoustic cavitation occurs when the acoustic intensity or pressure exceeds a threshold of the tissue (cavitation threshold).

The duration of each focused ultrasound wave may be less than 50 microseconds, for instance a few microseconds.

To this aim, the ultrasound probe 2 may for instance emit focused ultrasound waves that generate, at their focal spot, a peak negative pressure half-cycle that exceeds a peak negative pressure of 10 MPa. At their focal spot, the peak positive pressure half-cycle of the focused ultrasound waves may exceeds a peak positive pressure of 50 MPa.

An ultrasound probe 2 suited for emitting such high intensity controlled focused ultrasound waves is illustrated on FIG. 2.

In the illustrated embodiment, the ultrasound probe 2 comprises a reflective cavity 9 that may be filled with a liquid 10, for example water and in which the ultrasound transducers 6 are located.

The reflective cavity 9 comprises walls made of a material forming a highly reflective interface for acoustic waves, for example thin films separating the liquid contained in the cavity from the air outside the cavity.

The reflective cavity 9 is in contact at one of its ends with the patient P through a window 9a in the cavity wall, directly or through an acoustic lens 13 mounted on the window 9a.

The reflective cavity 9 comprises a multi-scattering medium 11 adapted to be traversed by acoustic waves emitted by the ultrasound transducers before said waves reaches the patient's body. The multi-scattering medium 11 is able to cause multiple scattering of said acoustic waves.

The multi-scattering medium 11 is located, for example, near the window 9a of the reflective cavity 9 and comprises a number of scatterers 12, for instance between several tens to several thousands of scatterers 12.

The scatterers 12 are adapted to scatter acoustic waves and are advantageously distributed randomly or non-periodically in the multi-scattering medium 11, meaning that their distribution does not exhibit a periodic structure. The scatterers 12 may thus exhibit a surface having a significant difference in impedance compared to the medium of the reflective cavity.

The scatterers 12 can have the general shape of vertical rods held in place by frames or attached to the walls of the reflective cavity. Alternatively, the scatterers 12 may take the form of beads, granules or cylinders and be held in place by foam, an elastomer, or three-dimensional frames so that they are distributed over all three dimensions of the space to form the multi-scattering medium 11.

The scatterers 12 may, for example, have transverse cross-sections that are substantially between 0.1 and 5 times the wavelength of the wave in the reflective cavity, for example between 0.5 and 1 times said wavelength. Said transverse cross-section is understood to be a cross-section taken perpendicularly to the extension direction of the scatterers 12 and/or to the longest extension direction of the multi-scattering medium 11.

The scatterers 12 can be distributed within the multi-scattering medium 11 so that their surface density in a cross-section of the multi-scattering medium 11 transverse to the extension direction Z of the scatterers 12, is, for an acoustic wave having a centre frequency of about 1 MHz, ten or so scatterers 12 per square centimetre, for example eighteen acoustic scatterers 12 per square centimetre.

In the case of a three-dimensional multi-scattering medium, the scatterers 12 can be distributed in the multi-scattering medium 11 so that their volume packing density within the multi-scattering medium 11 is between 1% and 30%.

The length of the multi-scattering medium 11, along the direction of propagation of the wave, may be a few centimetres, for example two centimetres.

The array 5 of ultrasound transducers 6 can be arranged on a face of the reflective cavity 9 facing the window open on the patient's body or may be oriented so as to emit waves toward the multi-scattering medium 11, at a certain angle relative to a cavity extension direction Y, for example 60°.

Such a reflective cavity 9 with a multi-scattering medium 11 forms a reverberator that permits, at the same time,
- to finely control the location of the focal spot of ultrasound waves emitted by the ultrasound probe 2, and
- to amplify the pressure of an acoustic wave generated by the ultrasound transducer array 6 by more than 20 dB.

Figure 4:
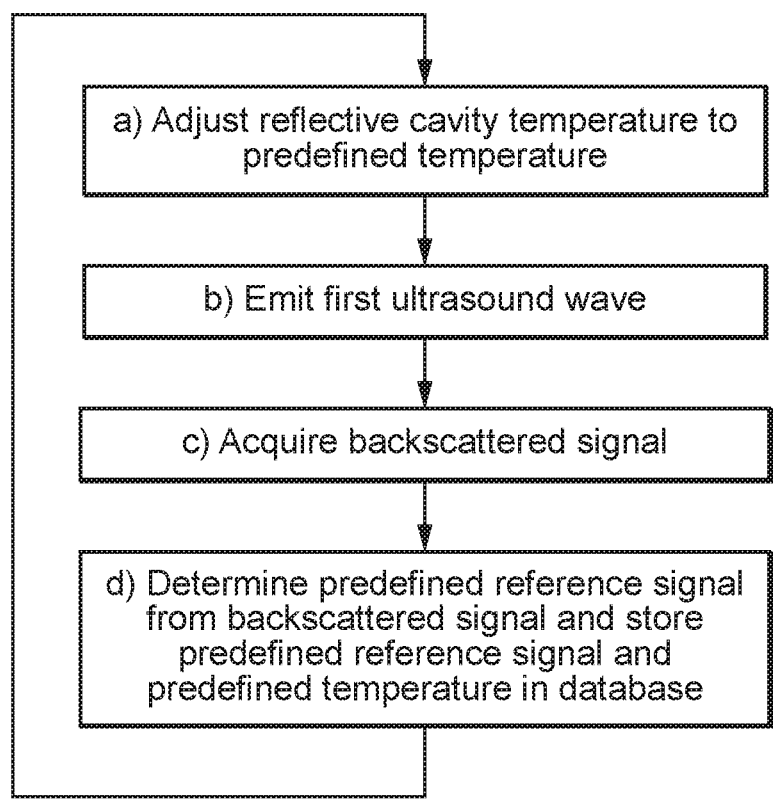
FIG. 4 is a flowchart of a method for calibrating a system for secure ultrasound treatment of living tissues according to an embodiment of the invention.

To this aim, prior to performing the method for secure ultrasound treatment of living tissues according to the invention, a calibration of the ultrasound probe 2 may be conducted in order to define predefined treatment signals and predefined emission signals as illustrated on FIGS. 2 and 4.

Such a calibration may involve the determination of matrix of individual emission signals eik(t) such that, to generate an ultrasound wave s(t) focused at a target point T of the treatment region R, each transducer i of the array 6 emits an emission signal:

$$S_i(t) = e_{ik}(t) \otimes s(t).$$

These individual emission signals may be determined by calculation (for example using a spatio-temporal inverse filter method), or may be determined experimentally during a preliminary learning step.

During an example of such a learning step, an ultrasonic pulse signal may be emitted by a hydrophone, successively placed at a succession of target points T in a volume of liquid placed in contact with the ultrasound probe 2. The signals $r_{ik}(t)$ received by each transducer i of the array 6 from the emission of said ultrasonic pulse signal are captured. The signals $r_{ik}(t)$ are then converted by the analog-to-digital converters and stored in the memory connected to the processor CPU, which then calculates the individual emission signals $e_{ik}(t)$ by time reversal of said received signals:

$$e_{ik}(t) = r_{ik}(-t).$$

When one or more focused ultrasound waves are then to be focused on a predetermined target point T within the treatment region R, the ultrasound probe 2 is placed in contact with the patient P, and an emission signal is emitted by each transducer i of the array 6:

$$S_i(t) = e_{ik}(t) \otimes s(t).$$

An ultrasound probe suitable for the invention may be optimized to focus ultrasound energy in a predefined region, called an electronically scannable region E illustrated on FIG. 2.

An electronically scannable region E is a region of the patient body where the focusing of ultrasound energy by the ultrasound probe is more efficient and/or is calibrated.

The electronically scannable region E may be predefined during the preliminary learning step mentioned. The electronically scannable region can for instance be defined by the succession of target points T where the hydrophone has been successively located during the preliminary learning step.

The predefined treatment signals, predefined emission signals and/or predefined reference signal may in particular be calibrated in function of the operating temperature.

It may thus be possible to predetermine a predefined treatment signal database associating predefined treatment signals with temperatures of the reflective cavity, a predefined emission signal database associating predefined emission signals with temperatures of the reflective cavity and/or a predefined reference signal database associating predefined reference signals with temperatures of the reflective cavity.

To this aim, a calibration process may be reiterated while adjusting the temperature of the reflective cavity to a plurality of predefined temperature.

As illustrated on FIG. 4, the invention thus also concerns a method for calibrating a system for secure ultrasound treatment of living tissues as detailed above. The method comprises the successive steps of:

a) adjusting a temperature of the reflective cavity to a predefined temperature, b) emitting at least one first ultrasound wave in the reflective cavity by controlling at least one transducer of the ultrasound probe, said first ultrasound wave generating a backscattered ultrasound wave in the reflective cavity, c) acquiring a backscattered signal in response to the backscattered ultrasound wave in the reflective cavity by controlling at least one transducer of the ultrasound probe, d) determining a predefined reference signal function of said backscattered signal and storing said predefined reference signal associated with the predefined temperature in a database associating predefined reference signals with temperatures of the reflective cavity.

The steps a) to d) may be performed several times for a respective plurality of predefined temperature in order to build a database associating predefined reference signals with a plurality of temperatures of the reflective cavity.

The steps a) to d) may also be performed several times for a respective plurality of predefined emission signals in order to build a database associating predefined reference signals with a plurality of predefined emission signals.

During step a), a controlled medium with an acoustic impedance comparable to the acoustic impedance of water may be located in contact with the ultrasound probe, in order to control the propagation of the ultrasound wave outside the reflecting cavity. This calibration medium can be a water-tank filled with water at constant temperature or a tissue mimicking phantom for acoustic experiments (as an example made of Poly Vynil Alcool PVA). The same method may be adapted to predetermine a predefined treatment signal database associating predefined treatment signals with temperatures of the reflective cavity and/or a predefined emission signal database associating predefined emission signals with temperatures of the reflective cavity.

The invention claimed is:

1. A system for secure ultrasound treatment of living tissues,
the system comprising:
an ultrasound probe comprising:
a reflective cavity in acoustic communication with living tissues to transmit ultrasound waves to said living tissues;
at least one transducer;
a thermometer for measuring a temperature of the reflective cavity; and
a controller configured to control the at least one transducer of the ultrasound probe, the controller configured to:
cause the at least one transducer to emit at least one first ultrasound wave in the reflective cavity by controlling the at least one transducer of the ultrasound probe, said first ultrasound wave generating a backscattered ultrasound wave in the reflective cavity;
cause the at least one transducer to acquire a backscattered signal in response to detecting the backscattered ultrasound wave in the reflective cavity;
determine whether an insonification can be safely performed by:
computing a similarity value between said backscattered signal and a predefined reference signal; and
comparing said similarity value with a security threshold to determine whether an insonification can be safely performed; and
cause the at least one transducer of the ultrasound probe to emit at least one second ultrasound wave in the reflective cavity to treat the living tissues if it is determined that an insonification can be safely performed, said at least one second ultrasound wave being transmitted to the living tissues, focused on at least one target point of the living tissues and generating a pressure pulse sufficient to result in cavitation at said at least one target point,
wherein the system is configured to select the predefined reference signal in a predefined reference signal database associating predefined reference signals with temperatures of the reflective cavity that are measured by the thermometer, and
wherein a multi-diffusing medium is located in the reflective cavity, the medium containing scatterers which cause a multiple scattering of the at least one first ultrasound wave and the second ultrasound wave.

2. The system according to claim 1, the system being configured to emit the at least one second ultrasound wave by driving the at least one transducer of the ultrasound probe with a predefined treatment signal,
and for selecting the predefined treatment signal in a predefined treatment signal database associating predefined treatment signals with temperatures of the reflective cavity.

3. The system according to claim 1, the system being configured so that said at least one first ultrasound wave does not generate a pressure pulse sufficient to result in cavitation in the living tissues.

4. The system according to claim 1, the system being configured so that said at least one first ultrasound wave is transmitted to the living tissues, focused on at least one target point of the living tissues, and configured so that said at least one first ultrasound wave generates a pressure pulse sufficient to result in cavitation at said at least one target point.

5. The system according to claim 4, the system being configured so that said similarity value between said backscattered signal and said predefined reference signal is indicative of a presence of forbidden tissues in a region of the living tissues penetrated by said at least one first ultrasound wave.

6. The system according to claim 4, the system being configured so that said predefined reference signal is indicative of a cavitation at said at least one target point of the living tissues resulting from a pressure pulse generated by said at least one first ultrasound wave.

7. The system according to claim 4, the system being configured so that said predefined reference signal is a function of a backscattered signal acquired in at least one previous insonification, said previous insonification is performed prior to the step of emitting at least one first ultrasound wave in the reflective cavity, said previous insonification comprising:

emitting at least one ultrasound wave in the reflective cavity by controlling at least one transducer of the ultrasound probe, said at least one ultrasound wave being transmitted to the living tissues and focused on at least one target point of the living tissues, said at least one ultrasound wave generating a backscattered ultrasound wave in the reflective cavity; and acquiring a backscattered signal in response to said backscattered ultrasound wave in the reflective cavity by controlling the at least one transducer of the ultrasound probe, wherein said predefined reference signal is a function of an average of a plurality of backscattered signals acquired from a respective plurality of previous insonifications.

8. The system according to claim 1, the system being configured so that the at least one second ultrasound wave is transmitted in the living tissues through a window formed in the reflective cavity.

9. The system according to claim 1, the system being configured so that the at least one second ultrasound wave is emitted by driving the at least one transducer of the ultrasound probe with a predefined treatment signal whose duration is less than 10 milliseconds, wherein the duration of said predefined treatment signal is at least 10 times longer than the duration of the pressure pulse generated by the second ultrasound wave at the at least one target point of the living tissues.

10. The system according to claim 1, wherein said at least one second ultrasound wave generates at the at least one target point of the living tissues a peak negative pressure half-cycle that exceeds a peak negative pressure of 5 MPa and/or a peak positive pressure half-cycle that exceeds a peak positive pressure of 20 MPa.

11. The system according to claim 1, the system being configured so that said treating the living tissues comprises controlling the at least one transducer of the ultrasound probe to successively emit a sequence of second ultrasound waves in the reflective cavity, said second ultrasound waves being transmitted to the living tissues, respectively focused on a plurality of respective target points of the living tissues, said second ultrasound waves being electronically steered to scan a treatment region of the living tissues formed by said plurality of target points.

12. The system according to claim 11, the system being configured so that a duration of a pressure pulse generated by each second ultrasound wave of the sequence of second ultrasound waves is less than 50 microseconds.

13. A method for calibrating a system for secure ultrasound treatment of living tissues according to claim 1, the method comprising putting the reflective cavity of the system in acoustic communication with living tissues;

the method further comprising at least the successive steps of:

adjusting a temperature of the reflective cavity to a predefined temperature;

emitting at least one first ultrasound wave in the reflective cavity by controlling the at least one transducer of the ultrasound probe of the system, said first ultrasound wave generating a backscattered ultrasound wave in the reflective cavity;

acquiring a backscattered signal in response to the backscattered ultrasound wave in the reflective cavity by controlling the at least one transducer of the ultrasound probe; and determining a predefined reference signal function of said backscattered signal and storing said predefined reference signal associated with the predefined temperature in a database associating predefined reference signals with temperatures of the reflective cavity.

14. A system for secure ultrasound treatment of living tissues, said system comprising:

an ultrasound probe comprising a reflective cavity in acoustic communication with living tissues to transmit ultrasound waves to said living tissues and at least one transducer;

a thermometer for measuring a temperature of the reflective cavity;

means for controlling the at least one transducer of the ultrasound probe to emit at least one first ultrasound wave in the reflective cavity, said first ultrasound wave generating a backscattered ultrasound wave in the reflective cavity;

means for controlling the at least one transducer of the ultrasound probe to acquire a backscattered signal in response to detecting the backscattered ultrasound wave in the reflective cavity;

means for determining whether an insonification can be safely performed by:

computing a similarity value between said backscattered signal and a predefined reference signal; and comparing said similarity value with a security threshold to determine whether an insonification can be safely performed; and means for controlling the at least one transducer of the ultrasound probe to emit at least one second ultrasound wave in the reflective cavity if it is determined that an insonification can be safely performed, said at least one second ultrasound wave being transmitted in the living tissues, focused on at least one target point of the living tissues and generating a pressure pulse sufficient to result in cavitation at said at least one target point, the system being configured to select the predefined reference signal in a predefined reference signal database associating predefined reference signals with temperatures of the reflective cavity that are measured by the thermometer, wherein a multi-diffusing medium is located in the reflective cavity, the medium containing scatterers which cause a multiple scattering of the at least one first ultrasound wave and the second ultrasound wave.

15. A method of operating the system of claim 1, the method comprising:

emitting at least one first ultrasound wave in the reflective cavity by controlling the at least one transducer of the ultrasound probe, the first ultrasound wave generating a backscattered ultrasound wave in the reflective cavity;

acquiring a backscattered signal in response to detecting the backscattered ultrasound wave in the reflective cavity;

computing a similarity value between the backscattered signal and a predefined reference signal;

comparing the similarity value with a security threshold to determine whether an insonification can be safely performed;

responsive to determining that the insonification can safely be performed, emitting at least one second ultrasound wave in the reflective cavity to treat the living tissues, said at least one second ultrasound wave being transmitted to the living tissues, focused on at least one target point of the living tissues and generating a pressure pulse sufficient to result in cavitation at said at least one target point.

* * * * *